United States Patent [19]

Kim

[11] Patent Number: 4,587,124

[45] Date of Patent: May 6, 1986

[54] COMPOSITION FOR TREATING CUTANEOUS WOUNDS

[76] Inventor: Tuk M. Kim, 2546 San Bruno Ave., San Francisco, Calif. 94134

[21] Appl. No.: 664,513

[22] Filed: Oct. 25, 1984

[51] Int. Cl.$^4$ .............................................. A61K 35/78
[52] U.S. Cl. ................................................... 424/195.1
[58] Field of Search ...................................... 424/195.1

[56] References Cited

PUBLICATIONS

Lewis, Medical Rotary, Wiley & Sons N.Y. 1977, pp. 162, 163, 349 and 350.

*Primary Examiner*—Albert T. Meyers
*Assistant Examiner*—John W. Rollins
*Attorney, Agent, or Firm*—Flehr, Hohbach, Test, Albritton & Herbert

[57] ABSTRACT

Novel compositions and a method is provided for treating cutaneous wounds by applying the heat-treated oil extract of fruit seed of *Strychnos ignatii* Berg thereto.

11 Claims, No Drawings

COMPOSITION FOR TREATING CUTANEOUS WOUNDS

The present invention is directed to novel pharmaceutical compositions for treatment of cutaneous wounds. In particular, the present invention is directed to compositions for the treatment of cuts, burns, abscesses and insect bites.

The compositions according to the present invention contain an extract from fruit seeds of the Southeast Asian tree species *Strychnos ignatii* Berg. In raw form, the fruit from this tree is poisonous, but raw, ground seeds of the fruit have been known to be used in low dosage (about 1 mg/dose) for internal uses for the treatment of various maladies, including stomach aches, diarrhea, intestinal parasites and malaria. When crushed the raw seeds have been used directly on cuts, abrasions and poisonous bites from snakes, scorpions and centipedes. However, uses of hot oil extracts of *Strychnos ignatii* Berg have heretofore been unknown for treatment of burns, cuts, abscesses and insect bites, and in particular such uses in the form of ointments and oils have heretofore been unknown. It is unexpected that extracts of *Strychnos ignatii* Berg would have such uses, particularly in oil and ointment form, since it has heretofore been believed that only the raw fruit is usable, and only in extremely low dosages in order to avoid the poisonous effects. However, according to the present invention, the fruit is extracted in situ with hot oil and solid residues are discarded, since it is the extract which is used.

It is therefore an object of the present invention to provide a method for treating cutaneous wounds including burns, cuts, abscesses and insect bites by the heat treated oil extract of the fruit seeds of *Strychnos ignatii* Berg in a pharmaceutically acceptable carrier.

It is a further object of the present invention to provide novel pharmaceutical compositions for the treatment of cutaneous wounds comprising a heat treated oil extract of fruit seeds of *Strychnos ignatii* Berg in a pharmaceutically acceptable carrier.

It is another object of the present invention to provide a process of producing a pharmaceutical composition containing a heat treated oil extract of fruit seeds of *Strychnos ignatii* Berg in a pharmaceutically acceptable carrier.

These objects will be apparent from the following description of the preferred embodiments.

The present invention provides a method for treating cutaneous wounds such as burns, cuts, abscesses and insect bites comprising the step of applying thereto a composition comprising heat treated oil extracts of fruit seeds of *Strychnos ignatii* Berg in a pharmaceutically acceptable carrier. Novel compositions are also provided containing heat treated oil extracts of *Strychnos ignatii* Berg, as well as methods for preparing such compositions.

To form the heat treated oil extract of the fruit seeds of *Strychnos ignatii* Berg according to the present invention, the raw fruit seeds are first heated in oil, such as a vegetable oil, which is also a pharmaceutically acceptable carrier, at a temperature above about 150° F. for a period of time sufficient to cause a change in the relative densities of between the oil and the raw seeds, such that the seeds are caused to darken and rise to the surface of the oil. Preferably, a vegetable oil will be used such that the raw seeds at room temperature will remain below the surface of the oil. Oils derived from animal fat may also be used. The heating for a sufficient period of time causes the relative densities between the oil and the seeds to change such that the fruit seeds will rise to the surface of the oil and the fruit seeds will darken in color. This is normally in the order of about 20 to 40 minutes when the oil is heated to the temperature above 150°, preferably at about 200° to 250° F. The preferred oils include vegetable oils such as cotton seed oil, peanut oil, soybean oil, sesame seed oil, sunflower seed oil, perilla seed oil, and the like.

A sufficient amount of oil should be used so that the seeds will become completely immersed in the oil. Preferably a ratio of fruit seeds to oil in the range of about 1:2 to 1.5:2 weight to volume may be used. Thus, 1,000 to 1,500 grams of raw fruit seeds may be mixed with about 2,000 cc of oil and heated until the seeds darken and rise to the surface of the oil. The seeds will then be separated from the oil by decantation, filtration or the like, and then the separated oil will be filtered to remove the particulate matter.

The resulting composition will be an oil, which also serves as the pharmaceutical carrier, containing the extract which has been heat treated. This oil may be used directly and applied to burns, particularly first and second degree burns, cuts, various types of abscesses, insect bites, or other cutaneous eruptions. In one preferred form, the oil may be formed into an ointment. For example, to the oil a sufficient amount of beeswax or other waxy material may be added to form a gel. In a particularly preferred embodiment about 10–20% by weight of beeswax is added to the oil composition to convert into an ointment. Other commonly acceptable pharmaceutical adjuvants may also be added such as preservatives, antimicrobial agents, and the like, provided that the adjuvants do not substantially reduce or otherwise interfere with the pharmaceutical activity of the extract.

While the frequency of application of the pharmaceutical compositions according to the present invention depend upon the degree of injury, type of injury and the degree of infection, if any, in usual circumstances the concentration of the active extract is approximately as prepared above utilizing 1 to 1.5 kilograms of raw seeds cooked in about 2 liters of oil. This may be applied in ointment form, the ointment being formed by the addition of 10–20% by weight of beeswax to the oil and applied on the average of 2 or 3 times per day. While not intending to be restricted by a particular theory of the invention, it is believed that the novel composition according to the present invention will accelerate metabolism in skin and the surrounding tissue.

Having described the preferred embodiment of the invention, the following examples are provided by way of illustration but are not intended to limit the invention.

EXAMPLE 1

One kilogram of raw seeds of *Strychnos ignatii* Berg is admixed in 2 liters of seed oil and boiled until the seeds turn black in color and float to the surface of the oil. The oil is allowed to cool and the seeds are separated by straining the oil through a strainer. The oil is then filtered to remove particulate matter. About 20% by weight of beeswax is added to the oil to form an ointment. A subject suffering from a burn caused by boiling water is treated with this ointment by applications of twice a day of the ointment. In 7 days the burn is healed without evidence of a scar.

EXAMPLE 2

The ointment described above in EXAMPLE 1 is utilized for treatment of sunburn in a subject and is applied twice after the occurrence of the sunburn.

EXAMPLE 3

Mosquito bites, cuts and abscesses are treated with the ointment described above in EXAMPLE 1 to alleviate irritation and to assist in healing of the skin.

It will be appreciated from the above description and following claims that various modifications may be made to the invention without departing from the scope thereof. It is intended that these various modifications will be within the scope of the present invention.

What is claimed is:

1. A method for treating cutaneous wounds comprising the step of applying thereto a composition comprising heat-treated oil extracts of fruit seeds of *Strychnos ignatii* Berg in a pharmaceutically acceptable carrier, said extracts formed by the steps of
    (a) heating fruit seeds of *Strychnos ignatii* Berg in an amount of a pharmaceutically acceptable vegetable oil sufficient to allow such seeds to be immersed therein at a temperature above 150° F. for a period of time sufficient to cause a change in the relative densities between said oil and said seeds such that said seeds are caused to darken and to rise to the surface of said oil;
    (b) separating said seeds from said oil;
    (c) filtering the separated oil to form said composition.

2. A method according to claim 1 wherein said cutaneous wounds are selected from burns, cuts, abcesses and insect bites.

3. A method according to claim 1 wherein said composition consists essentially of said oil.

4. A method according to claim 1 wherein said composition is an ointment consisting essentially of 10-20% by weight of beeswax and 90-80% by weight of said oil.

5. A process for producing a pharmaceutical composition comprising the steps of
    (a) heating fruit seeds of *Strychnose ignatii* Berg in an amount of a pharmaceutically acceptable vegetable oil sufficient to allow said seeds to be immersed therein at a temperature about 150° F. for a period of time sufficient to cause a change in the relative densities between said oil and said seeds such that said seeds are caused to darken and to rise to the surface of said oil;
    (b) separating said seeds from said oil;
    (c) filtering the separated oil to form an oil composition comprising heat-treated oil extracts of *Strychnos ignatii* Berg in a vegetable oil carrier.

6. A process according to claim 5 wherein said oil is selected from the group consisting of oil derived from animal fat, cotton seed oil, peanut oil, soybean oil, sesame seed oil, sunflower seed oil and perilla seed oil.

7. A process according to claim 5 further comprising the step of (d) adding a sufficient amount of beeswax to the oil composition from step (c) to form an ointment comprising 10-20% by weight of beeswax.

8. A process according to claim 5 wherein in step (a) the ratio of said seeds to said oil is in a range of about 1:2 to 1.5:2 weight to volume.

9. A pharmaceutical composition prepared by the process of claim 5.

10. A composition according to claim 9 wherein said composition consists essentially of said oil.

11. A composition according to claim 9 wherein said composition is an ointment consisting essentially of 10-20% by weight of beeswax and 90-80% by weight of said oil.

* * * * *